United States Patent
Lu et al.

(10) Patent No.: US 11,530,426 B2
(45) Date of Patent: Dec. 20, 2022

(54) METHOD FOR BIOHYDROGEN PRODUCTION

(71) Applicant: Henan Agricultural University, Zhengzhou (CN)

(72) Inventors: Chaoyang Lu, Zhengzhou (CN); Quanguo Zhang, Zhengzhou (CN); Zhiping Zhang, Zhengzhou (CN); Danping Jiang, Zhengzhou (CN); Yanyan Jing, Zhengzhou (CN); Yi Wang, Zhengzhou (CN); Kaixin Wang, Zhengzhou (CN); Siyi Guo, Zhengzhou (CN); Jian Wang, Zhengzhou (CN)

(73) Assignee: HENAN AGRICULTURAL UNIVERSITY, Zhengzhou (CN)

( * ) Notice: Subject to any disclaimer, the term of this patent is extended or adjusted under 35 U.S.C. 154(b) by 0 days.

(21) Appl. No.: 17/232,223

(22) Filed: Apr. 16, 2021

(65) Prior Publication Data

US 2021/0324421 A1 Oct. 21, 2021

(30) Foreign Application Priority Data

Apr. 17, 2020 (CN) .......................... 202010305121.2

(51) Int. Cl.
| | | |
|---|---|---|
| *C12P 7/40* | (2006.01) | |
| *C12P 1/00* | (2006.01) | |
| *C12P 3/00* | (2006.01) | |
| *C25B 1/02* | (2006.01) | |

(52) U.S. Cl.
CPC ................... *C12P 3/00* (2013.01); *C12P 7/40* (2013.01); *C25B 1/02* (2013.01)

(58) Field of Classification Search
CPC ........... C12P 39/00; C12P 19/02; C12P 19/14; C12N 1/20; C12Y 302/01004; C25B 1/02
USPC ..................................... 435/243, 183, 252.1
See application file for complete search history.

(56) References Cited

FOREIGN PATENT DOCUMENTS

CN 109929897 * 6/2019 .............. C12P 39/00

OTHER PUBLICATIONS

Published CN109929897 2019, p. 1-2.*

* cited by examiner

*Primary Examiner* — Tekchand Saidha
*Assistant Examiner* — Mohammad Y Meah
(74) *Attorney, Agent, or Firm* — Matthias Scholl P.C.; Matthias Scholl (57) ABSTRACT

The disclosure provides a method for biohydrogen production. The method includes: mixing a hydrogen production medium and a buffer solution $Na_2HPO_4/NaH_2PO_4$ having a pH value of 5-9, to yield a first mixture; adding corn stalk powder and cellulase to the first mixture and mixing, to yield a second mixture; adding a suspension of photosynthesis bacteria HAU-M1 at the late exponential phase to the second mixture, to yield a third mixture; and sealing the third mixture and allowing for photo-fermentation biohydrogen production under anaerobic fermentation conditions.

12 Claims, 12 Drawing Sheets

METHOD FOR BIOHYDROGEN PRODUCTION

CROSS-REFERENCE TO RELATED APPLICATIONS

Pursuant to 35 U.S.C. § 119 and the Paris Convention Treaty, this application claims foreign priority to Chinese Patent Application No. 202010305121.2 filed Apr. 17, 2020, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to the field of photo-fermentation biohydrogen production, and more particularly, to a method for biohydrogen production.

Conventionally, hydrogen is mainly produced by electrolyzing water and reforming natural gas, but these methods consume lots of non-renewable energy source.

Biohydrogen production is an ideal route, as it degrades biomass, industrial wastewater, kitchen waste, etc., and generates hydrogen through metabolism. The method is friendly to a variety of substrates and has a high substrate conversion rate. However, the pH value of the fermentation broth in the photo-fermentation biohydrogen production process decreased quickly. The decrease of the pH value destroys the bacterial growth environment, leading to the death of bacteria, undesirable hydrogen production performance, and a low yield of hydrogen.

In existing passive saccharification and fermentation process, a citric acid buffer is used for enzymolysis of corn stalk with cellulase, thus ensuring a pH of the enzymatic hydrolysate is maintained at 4.8. After enzymatic hydrolysis, the pH is adjusted to 7 for photo-fermentation biohydrogen production. In this method, the enzymatic hydrolysis and hydrogen production are performed separately, which is time-consuming and energy consuming, leading to a low yield of hydrogen.

SUMMARY

The disclosure provides a method for biohydrogen production.

The method comprises: mixing a hydrogen production medium and a buffer solution of $Na_2HPO_4/NaH_2PO_4$ having a pH value of 5-9, to yield a first mixture; adding corn stalk powder and cellulase to the first mixture and mixing, to yield a second mixture; adding a suspension of photosynthesis bacteria HAU-M1 at the late exponential phase to the second mixture, to yield a third mixture; and sealing the third mixture and allowing for photo-fermentation biohydrogen production under anaerobic fermentation conditions.

In a class of this embodiment, the volume of the $Na_2HPO_4/NaH_2PO_4$ buffer is 110-130 mL, and the dry weight of the corn stalk powder is 5 g. Preferably, a pH of the $Na_2HPO_4/NaH_2PO_4$ buffer is 6.

In a class of this embodiment, the hydrogen production medium comprises 0.4 g/L $NH_4Cl$, 0.5 g/L $K_2HPO_4$, 2 g/L NaCl, 0.1 g/L yeast extract, 0.2 g/L $MgCl_2$, and 3.56 g/L sodium glutamate.

In a class of this embodiment, the cellulase is a liquid enzyme preparation; the cellulase has a volume of 4-6 mL and exhibits enzyme activity of 51 FPU/mL; the suspension of HAU-M1 photosynthesis bacteria has a volume of 20-40 mL. The suspension of HAU-M1 photosynthesis bacteria comprises *Rhodospirillum cristatum*, *Rhodopseudomonas capsulatus*, *Rhodopseudomonas palustris*, *Rhodobacter sphaeroides*, and *Rhodobacter capsularis*.

The *Rhodospirillum cristatum*, *Rhodopseudomonas capsulatus*, *Rhodopseudomonas palustris*, *Rhodobacter sphaeroides*, and *Rhodobacter capsularis* are mixed in a volume ratio of 27:25:28:9:11; the number of viable *Rhodospirillum cristatum* in the suspension is $12.0 \times 10^8$ cells/mL; the number of viable *Rhodopseudomonas capsulatus* in the suspension is $11.0 \times 10^8$ cells/mL; the number of viable *Rhodopseudomonas palustris* in the suspension is $12.5 \times 10^8$ cells/mL; the number of viable *Rhodobacter sphaeroides* in the suspension is $4.0 \times 10^8$ cells/mL; and the number of viable *Rhodobacter capsularis* in the suspension is $5.0 \times 10^8$ cells/mL.

In a class of this embodiment, the photo-fermentation biohydrogen production is carried out at a temperature of 28-32° C. and a light intensity of 2800-3200 Lux, and more preferably, at a temperature of 30° C. and a light intensity of 3000 Lux.

To shorten the overall time of the photo-fermentation reaction (involving enzymatic hydrolysis and biohydrogen production), the fermentation solution for biohydrogen productions has a certain range of concentrations, and the enzymatic hydrolysis, saccharification, and hydrogen production are simultaneously carried out.

The following advantages are associated with the method of the disclosure:

The disclosure uses corn stalk as a substrate and uses a $Na_2HPO_4/NaH_2PO_4$ buffer to produce a high yield of hydrogen from photosynthetic organisms. The disclosure also probes into the effect of buffers with different initial pH values on the biohydrogen productions, analyzes the changes in the hydrogen content, hydrogen production rate, cumulative hydrogen production, reducing sugar concentration, pH value of buffer solution, and soluble metabolites, calculates the kinetics of biohydrogen production, and probes into the effect of different initial pH values on the characteristics of the hydrogen-producing liquid and gas, and probes into the effect of different pH values on the kinetic characteristics of biohydrogen production.

BRIEF DESCRIPTION OF THE DRAWINGS

FIGS. 1A-AE are line graphs illustrating the effect of pH values of buffer solution on photo-fermentation biohydrogen production according to one embodiment of the disclosure; wherein

FIGS. 2A-2F are bar graphs illustrating the effect of pH values of buffer solution on soluble metabolites; in FIG. 2A, pH=5; in FIG. 2B, pH=5.5; in FIG. 2C, pH=6; in FIG. 2D, pH=6.5; in FIG. 2E, pH=7; in FIG. 2F, Control group (abbreviated to CG)

DETAILED DESCRIPTION

To further illustrate the disclosure, embodiments detailing a method for biohydrogen production are described below.

It should be noted that the following embodiments are intended to describe and not to limit the disclosure.

Example 1

1. Materials and Methods

1.1 Microorganisms and Substrate

Photosynthesis bacteria HAU-M1 were capable of degrading organic matter at different light intensities to produce hydrogen, and were obtained using the method (Han Binxu. Isolation and identification of photosynthetic bacteria and analysis of its biohydrogen production characteristics [D]. Henan Agricultural University, 2011). A suspension of the photosynthesis bacteria HAU-M1 comprised *Rhodospirillum cristatum, Rhodopseudomonas capsulatus, Rhodopseudomonas palustris, Rhodobacter sphaeroides,* and *Rhodobacter capsularis*, which were mixed in a volume ratio of 27:25:28:9:11; the number of viable *Rhodospirillum cristatum* in the suspension was $12.0 \times 10^8$ cells/mL; the number of viable *Rhodopseudomonas capsulatus* in the suspension was $11.0 \times 10^8$ cells/mL; the number of viable *Rhodopseudomonas palustris* in the suspension was $12.5 \times 10^8$ cells/mL; the number of viable *Rhodobacter sphaeroides* in the suspension was $4.0 \times 10^8$ cells/mL; and the number of viable *Rhodobacter capsularis* in the suspension was $5.0 \times 10^8$ cells/mL.

1.2 Medium and Buffer Solution

By using prior art methods, the photosynthesis bacteria HAU-M1 were cultured in a culture medium until the late logarithmic phase; referring to Table 1, the culture medium contained 0.5 g/L $NH_4Cl$, 0.1 g/L $K_2HPO_4$, 1 g/L NaCl, 0.5 g/L yeast extract, 0.1 g/L $MgSO_4$, 2.0 g/L $CH_3COONa$, and 1 g/L $NaHCO_3$.

Referring to Table 1, a biohydrogen production medium contained 0.4 g/L $NH_4Cl$, 0.5 g/L $K_2HPO_4$, 2 g/L NaCl, 0.1 g/L yeast extract, 0.2 g/L $MgCl_2$, and 3.56 g/L sodium glutamate, all of which were dissolved in pure water.

TABLE 1

| Culture medium (g/L) | | Biohydrogen production medium (g/L) | | Buffer solution (g/L) | | |
|---|---|---|---|---|---|---|
| $NH_4Cl$ | 0.5 | $NH_4Cl$ | 0.4 | pH value | $Na_2HPO_4$ | $NaH_2PO_4$ |
| $K_2HPO_4$ | 0.1 | $K_2HPO_4$ | 0.5 | 5 | 0.0890 | 11.9248 |
| NaCl | 1 | NaCl | 2 | 5.5 | 0.2778 | 11.7653 |
| Yeast extract | 0.5 | Yeast extract | 0.1 | 6 | 0.8428 | 11.2878 |
| $MgSO_4 \cdot 7H_2O$ | 0.1 | $MgCl_2$ | 0.2 | 6.5 | 2.3620 | 10.0039 |
| $CH_3COONa$ | 2 | Sodium glutamate | 3.56 | 7 | 5.4935 | 7.3576 |
| $NaHCO_3$ | 1 | — | — | Control group | 0.0563 | 11.9524 |

Corn stalk powder was provided by the Science and Education Park of Henan Agricultural University, which comprised cellulose, hemicellulose, and lignin, in a ratio of 39.23%, 31, 34%, and 10.35%. Total solids (TS) and volatile solids (VS) were 96.14% and 93.67%, respectively.

The cellulase was Cellulase Ctec2 that was a liquid enzyme preparation provided by Novozymes Biotechnology Co., Ltd. The cellulase had a volume of 20 mL and exhibited enzyme activity of 51 FPU/mL.

The pH values of the buffer solution were adjusted according to Equation (1):

$$pH = pK_{a2}^{\ominus} - lg(C(NaH_2PO_4)/C(Na_2HPO_4)) \quad (1)$$

1.3 Experimental Procedures:

A 180 mL erlenmeyer flask was used as a hydrogen production reactor, offering an effective volume of 150 mL. 120 mL of buffer solutions with different pH values (5, 5.5, 6, 6.5, 7, and control group) were separately added to the erlenmeyer flask. The pH value of the buffer solution of the control group was adjusted from 4.8 to 7 with NaOH. Referring to Table 1, the components of the biohydrogen production medium were added to the erlenmeyer flask and shaken evenly, followed by addition of 5 g of corn stalk powder. After shaking, 5 mL of cellulase was added to the erlenmeyer flask and shaken evenly. 30 mL of photosynthesis bacteria HAU-M1 at the late exponential phase was added to the erlenmeyer flask and shaken evenly. The erlenmeyer flask was sealed with a rubber slug and aerated with nitrogen to keep the anaerobic fermentation environment. The erlenmeyer flask was placed in an incubator at 30° C. and 3000 Lux and the amount of hydrogen produced was quantified every 24 hours.

1.4 Testing Method:

Hydrogen content was determined by a gas chromatography (6820 GC-14B, Agilent). Volatile fatty acids (VFAs) were measured by a gas chromatography-mass spectroscopy (7890B, Agilent, USA). pH value was measured with a pH meter (PHS-3E pH, Shanghai Youke Instrument Co., Ltd.). Reducing sugar concentration was determined by a 721 spectrophotometer with dinitrosalicylic acid method (DNS). Light intensity was determined by an illuminance meter (1010A, Shenzhen Shengli High Electronic Technology Co., Ltd.).

1.5 Analytical Methods

Kinetic parameters were calculated by modified Gompertz equation:

$$H = P\exp\left\{-\exp\left[\frac{R_m e}{P}(\lambda - t) + 1\right]\right\} \quad (2)$$

where, H is the cumulative hydrogen production (mL), P is the maximum potential hydrogen production (mL), Rm is the maximum hydrogen production rate (mL/h), $\lambda$ is the delay time (h), t is the time (h), e is the natural constant of 2.718. P, Rm and $\lambda$ are calculated by 1stOpt 15PRO software. An average hydrogen production rate was used to assess the overall hydrogen production rate of photosynthetic organisms.

$$R_{overall} = \frac{P}{(P/R_m) + \lambda} \cdot \frac{1}{V} \quad (3)$$

where, V is the working volume of the reactor, P is the maximum potential hydrogen production (mL), Rm is the maximum hydrogen production rate (mL/h), and $\lambda$ is the lag time (h).

The significance of pH values of buffers on the biohydrogen production was estimated by one-way ANOVA.

Energy conversion efficiency of photo-fermentation biohydrogen production was calculated by Equation (4):

$$E = \frac{V_{H_2} \times Q_{H_2}}{Q_{CS} \times m} \times 100\% \quad (4)$$

E is the energy conversion efficiency (%), $V_{H_2}$ is the cumulative hydrogen production (mL), $Q_{H_2}$ is the calorific value of hydrogen (12.86 J/mL), $Q_{CS}$ is the calorific value (17340.50 J/g) of corn stalk powder, m is the dry weight of corn stalk powder (g).

2. Results and Analysis 2.1 Effect of Buffer on Biohydrogen Production.

Figure 1A:
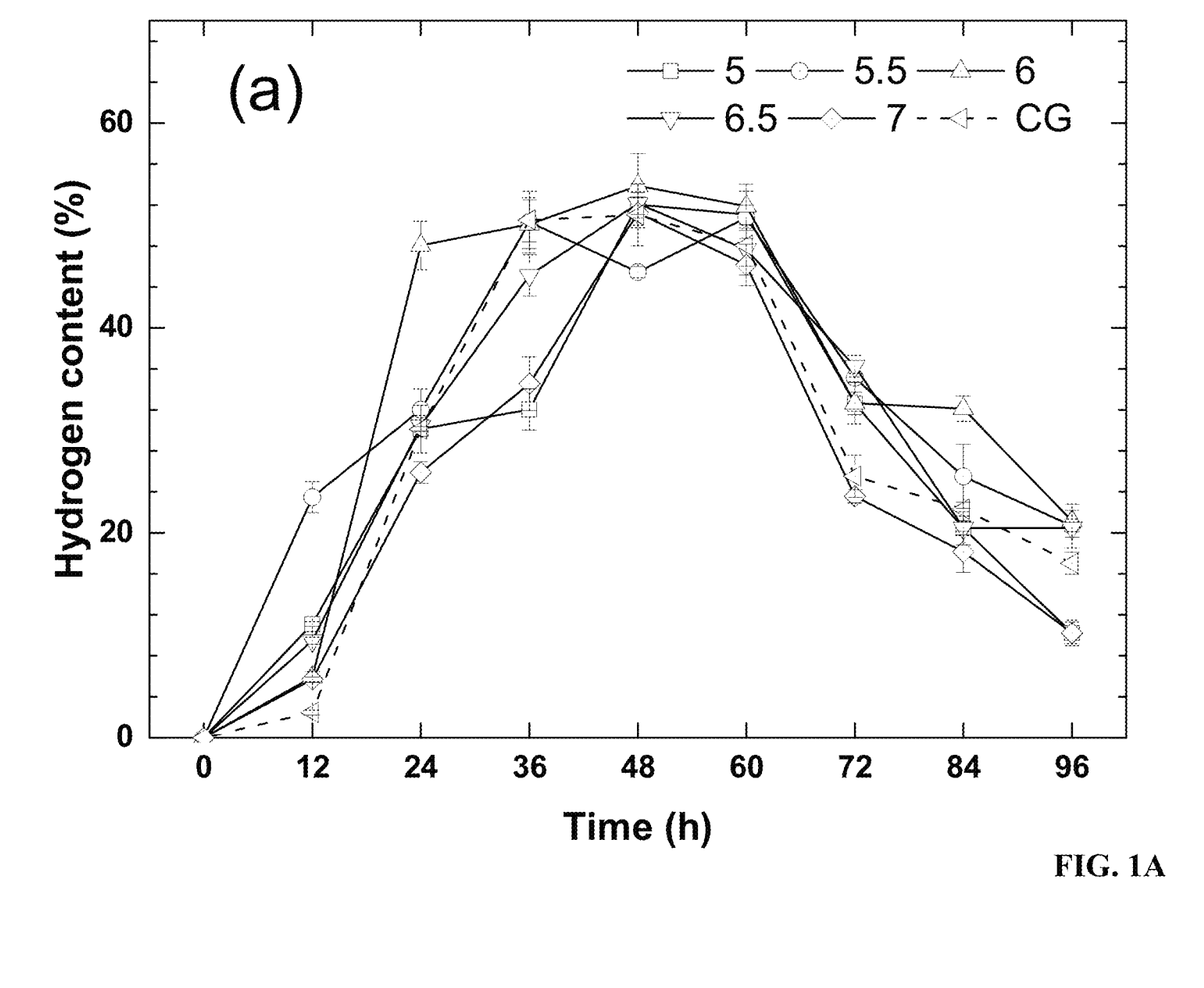
FIG. 1A shows hydrogen content.

Referring to FIG. 1A, the hydrogen content increases as the reaction proceeds, achieves peak value during 36-60 h, achieves maximum hydrogen content of 53.88% at 48 h and pH 6, and decreases drastically. The maximum hydrogen contents of 53.88% is higher than 52.06% obtained in the control group. Variations in hydrogen content were due to the metabolism pathway of the photosynthesis bacteria HAU-M1. The hydrogen contents obtained from the metabolic pathway of acetic acid and butyric acid are 66.67% and 50%, respectively. The ethanol type metabolic pathway only produces carbon dioxide, while the propionic acid type metabolic pathway consumes hydrogen. The hydrogen contents of biohydrogen production from acetic acid and butyric acid are 66.67% and 71.43%, respectively. The main metabolism pathways are the generation and consumption of acetic acid and butyric acid during the peak period of photo-fermentation biohydrogen production. Photo-fermentation biohydrogen production is a complex biochemical metabolic activity, which is also confirmed by the soluble metabolic components shown in FIGS. 2A-2F.

Chemical equations 5-7 are biohydrogen production by using acetic acid, propionic acid, and butyric acid-type metabolic, respectively. Chemical equation 8 is the ethanol metabolism. Chemical equations 9 and 10 are biohydrogen production by using acetic acid and butyric acid.

$$C_6H_{12}O_6 + 2H_2O \rightarrow 2C_2H_4O_2 + 2CO_2 + 4H_2 \quad (5)$$

$$C_6H_{12}O_6 + 2H_2 \rightarrow 2C_3H_6O_2 + 2H_2O \quad (6)$$

$$C_6H_{12}O_6 \rightarrow C_4H_8O_2 + 2CO_2 + 2H_2 \quad (7)$$

$$C_6H_{12}O_6 \rightarrow C_2H_6O + 2CO_2 \quad (8)$$

$$C_2H_4O_2 + 2H_2O \rightarrow 4H_2 + 2CO_2 \quad (9)$$

$$C_4H_8O_2 + 6H_2O \rightarrow 10H_2 + 4CO_2 \quad (10)$$

Figure 1B:
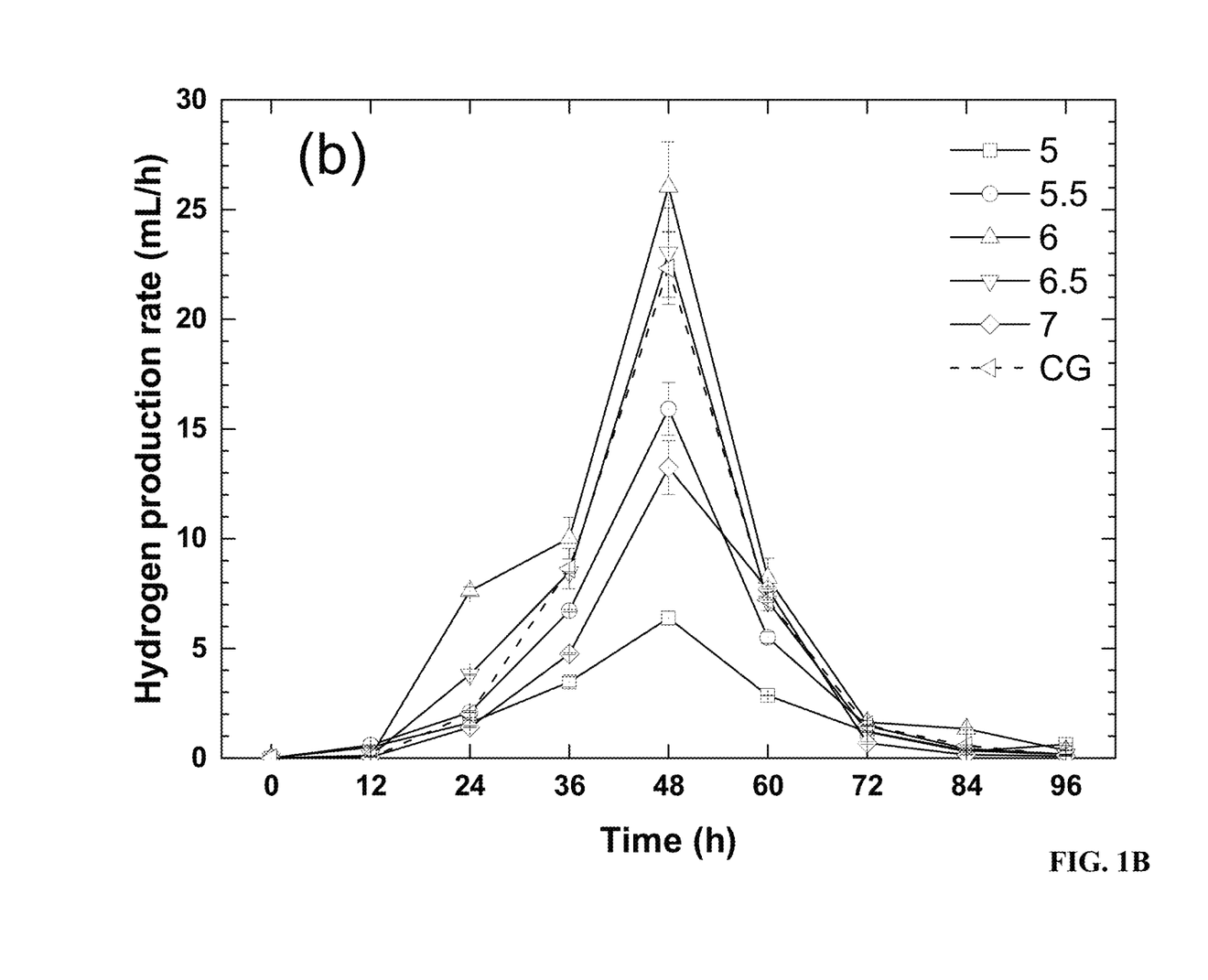
FIG. 1B shows hydrogen production rate.

Referring to FIG. 1B, the hydrogen production rates show a similar normal distribution with time. Hydrogen production rates are relatively low during 0-12 h, because the photosynthesis bacteria HAU-M1 are adapting to fermentation broth. Hydrogen production rates decreases in the latter period due to the odious growing environment caused by accumulation of inhibitors. At 48 h, the hydrogen production rates achieve peak values in the reaction solutions with different initial pH values. With the increase of the initial pH values, the maximum hydrogen production rate increases, achieves peak value of 26.04 mL/h at pH value of 6, and then decreases.

Figure 1C:
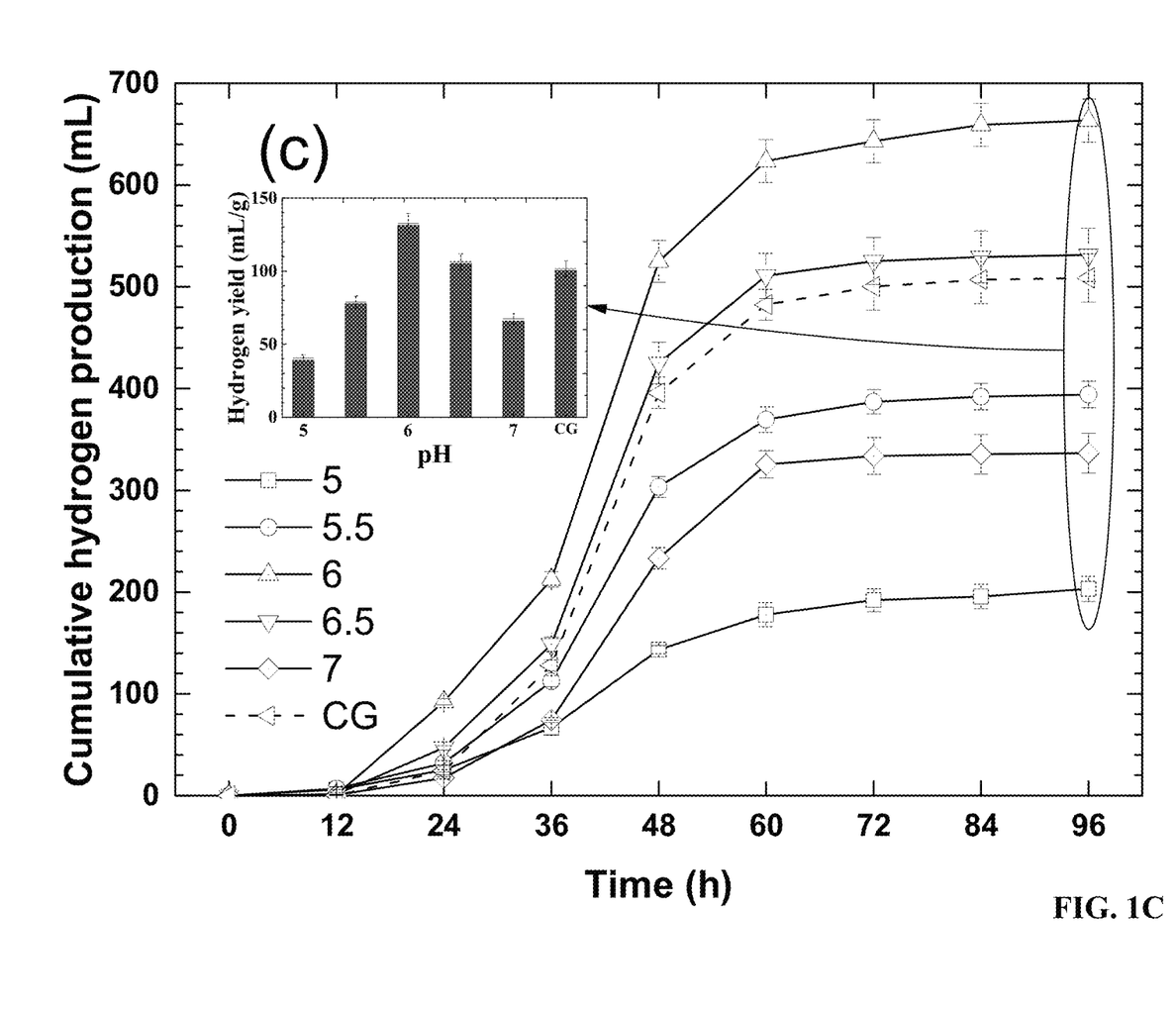
FIG. 1C shows cumulative hydrogen production.

Referring to FIG. 1C, the cumulative hydrogen production show continuous growth trend with time. Exponential growth of the hydrogen production yield is achieved during 36-48 h, which was consistent with the logarithmic growth model of photosynthetic bacteria, indicating that the explosive growth of photosynthetic bacteria enhances the biohydrogen production yield. Variety in cumulative hydrogen production is related to the wandering pH values between appropriate pH values of the cellulase (4.8) and the photosynthetic bacteria (7.0). The cumulative hydrogen production increases, reaches the maximum value at pH 6, and then decreases when pH values of buffer solution increases from 5-7. The cumulative hydrogen production of 132.69 mL/g observed in the experimental group at pH value of 6 is higher than 101.73 mL/g observed in the control group. It is because the pH value of the control group is adjusted from 4.8 to 7 by using NaOH, so the buffer capacity is not as good as the experimental group, where pH values are directly adjusted to specific pH values by using buffer salt. Stable buffer environment guaranteed the efficient biohydrogen production of photosynthetic bacteria.

Figure 1D:
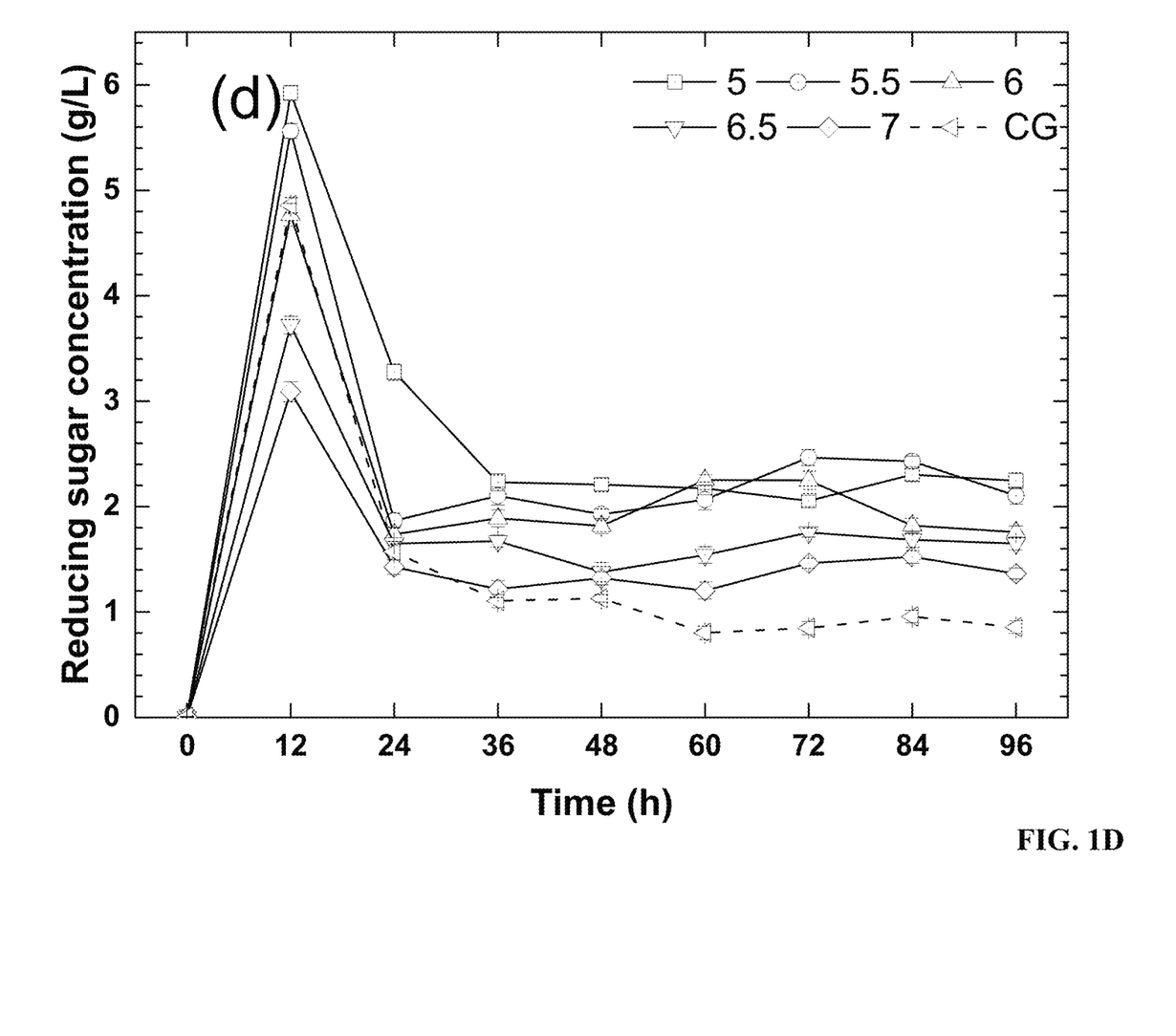
FIG. 1D shows reducing sugar concentration.

Referring to FIG. 1D, as the biohydrogen production reaction proceeds, the reducing sugar concentration increases rapidly and then decreases drastically. In 0-12 hours, the photosynthetic bacteria HAU-M1 are adapting to the fermentation broth and sugar is not utilized by the photosynthetic bacteria HAU-M1. During 12-24 h, the reducing sugar is used to produce hydrogen, which leads to the decrease in reducing sugar concentration. The rate of sugar production from corn stalk is equal to the rate of sugar utilized by the photosynthetic bacteria in stable period (24-36 h). The closer the pH is to 4.8, the greater the concentration of reducing sugar.

Figure 1E:
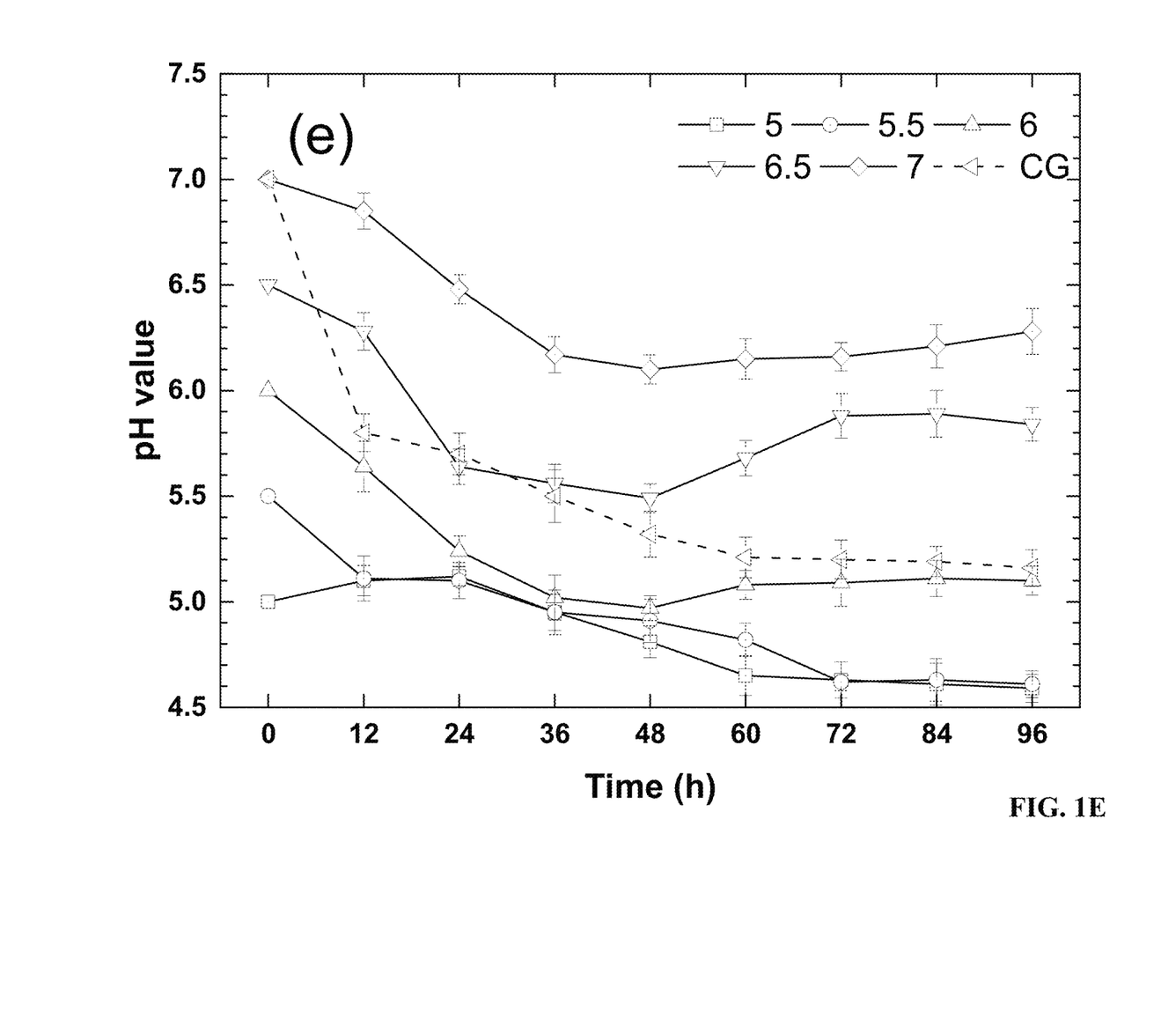
FIG. 1E shows pH value of the buffer solution.
Figure 2A:
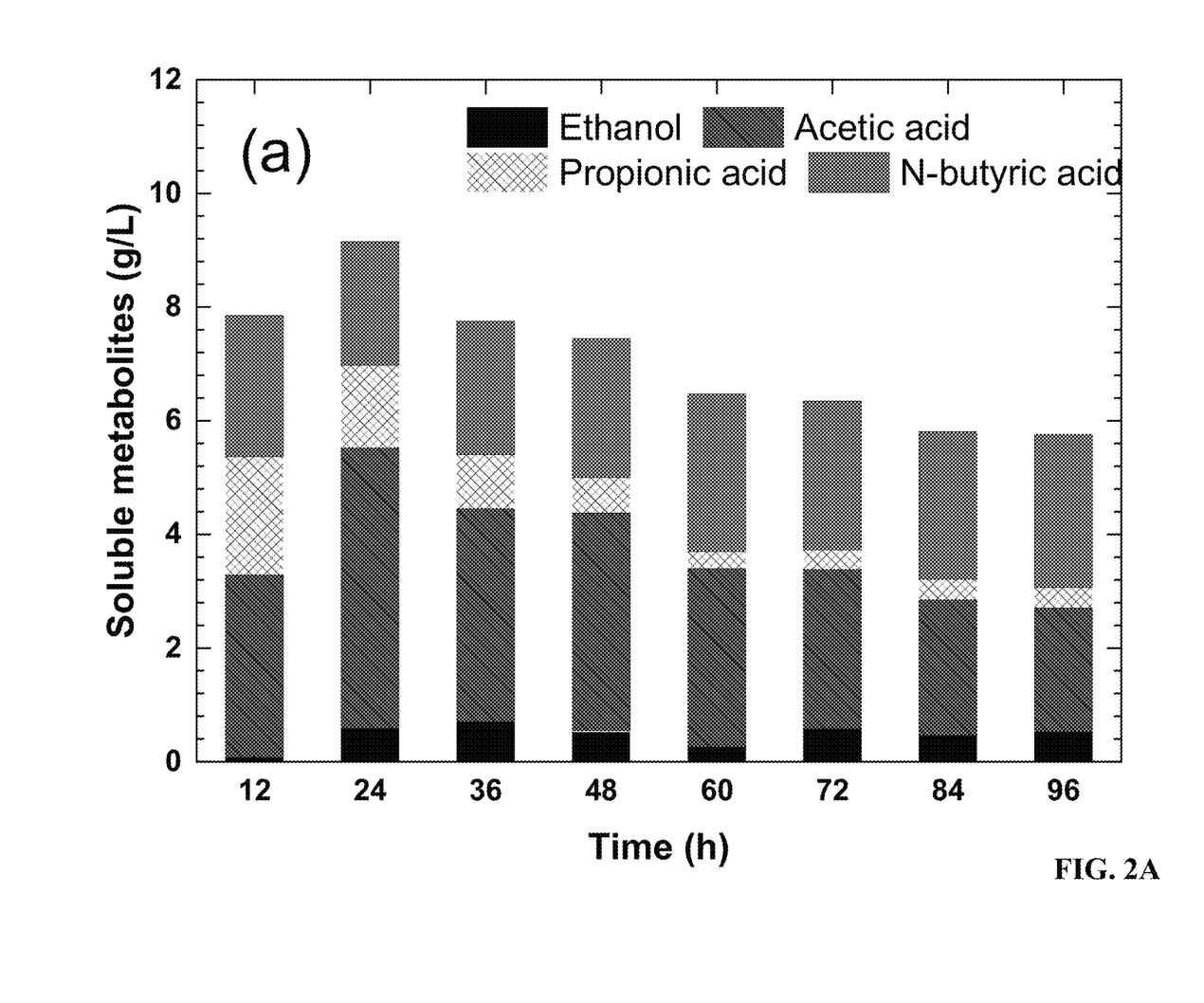
Figure 2B:
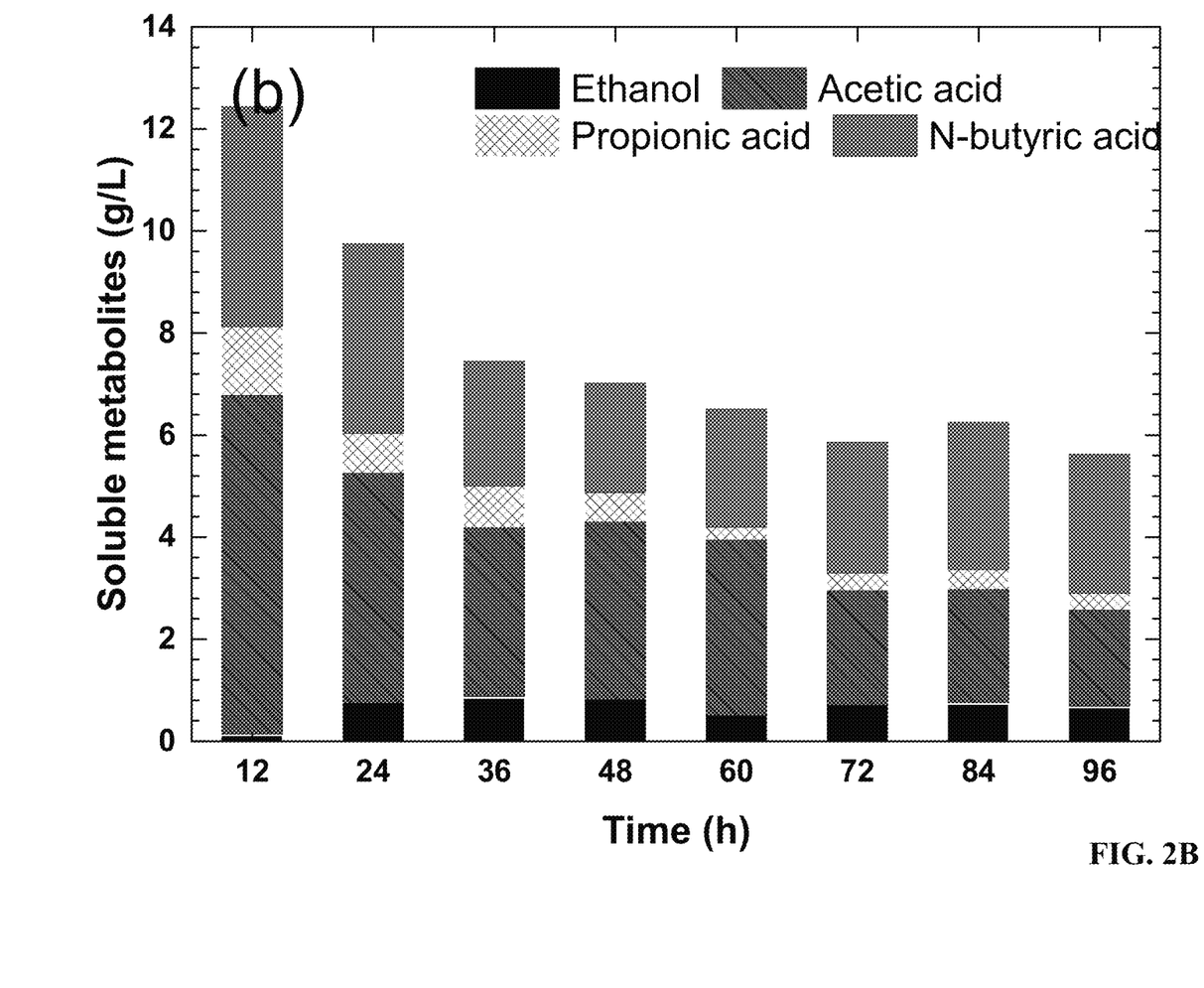
Figure 2C:
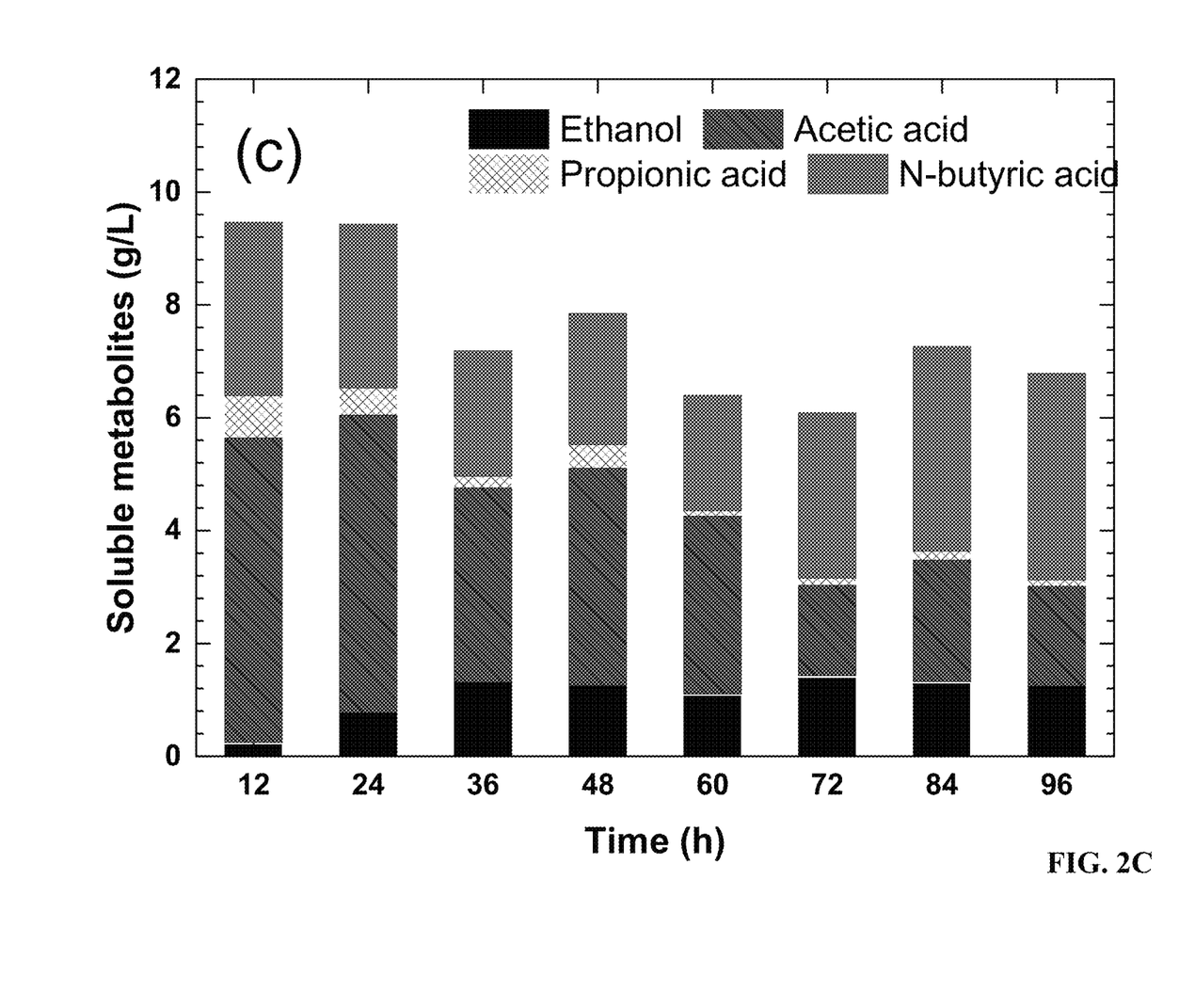
Figure 2D:
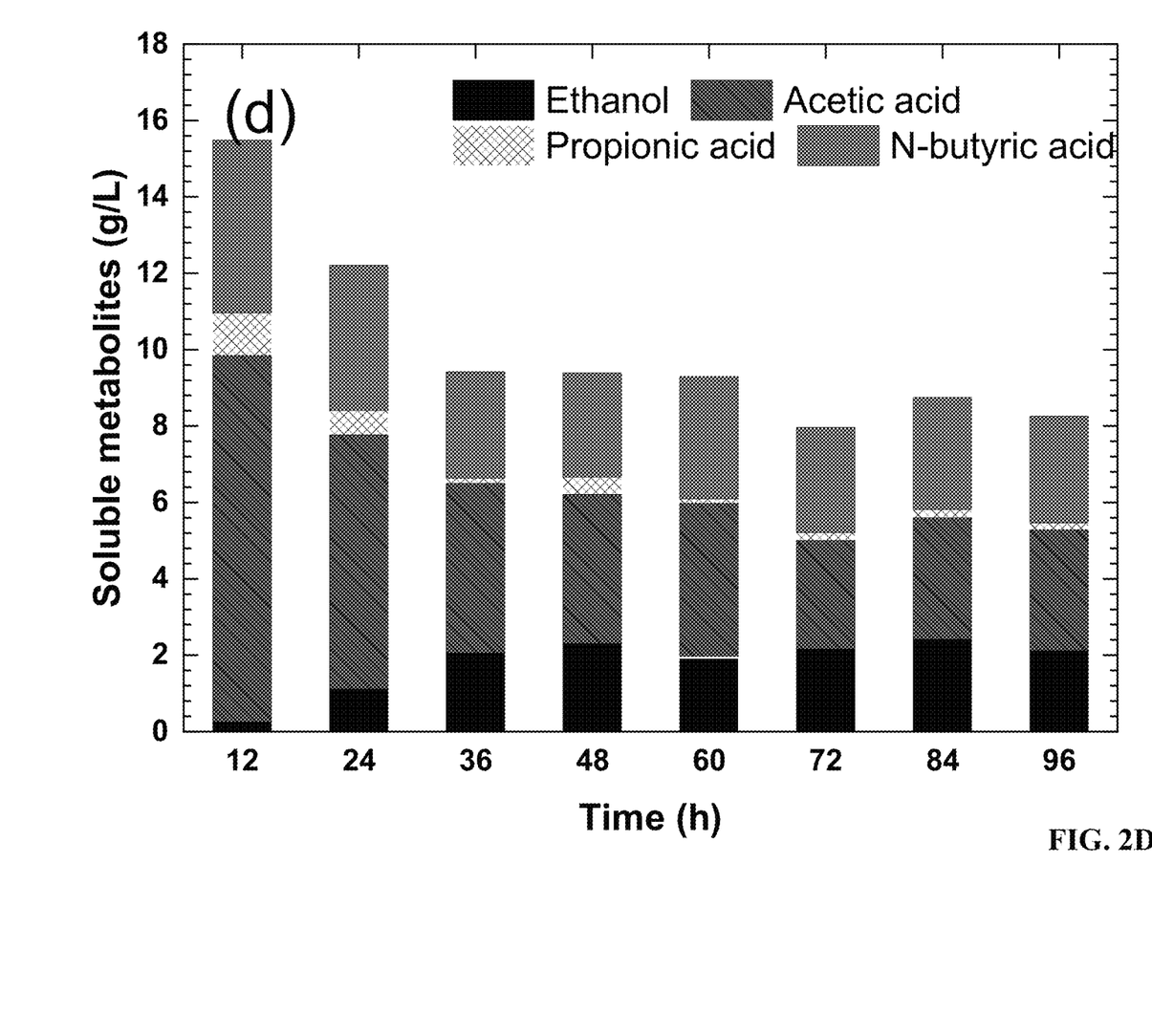
Figure 2E:
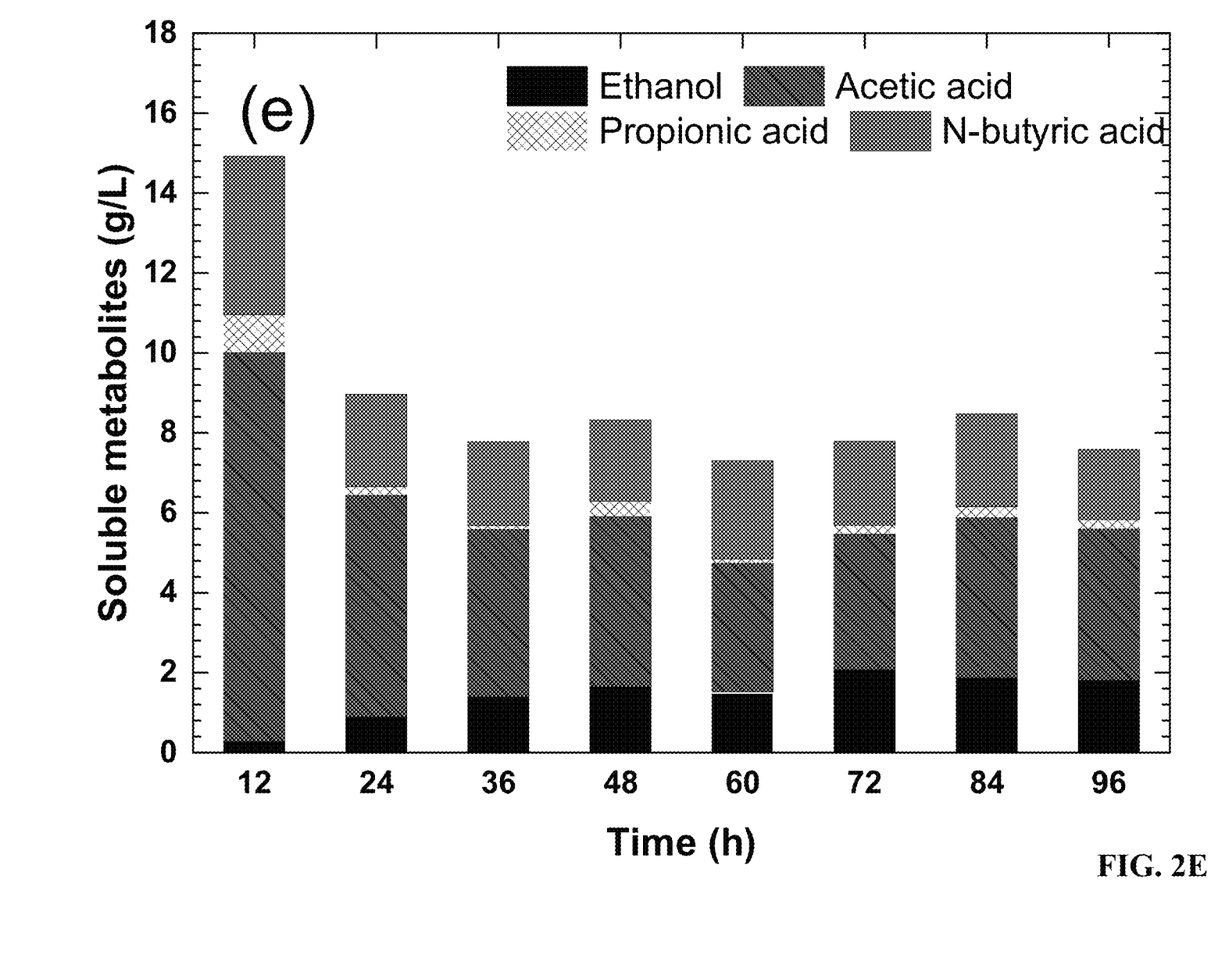
Figure 2F:
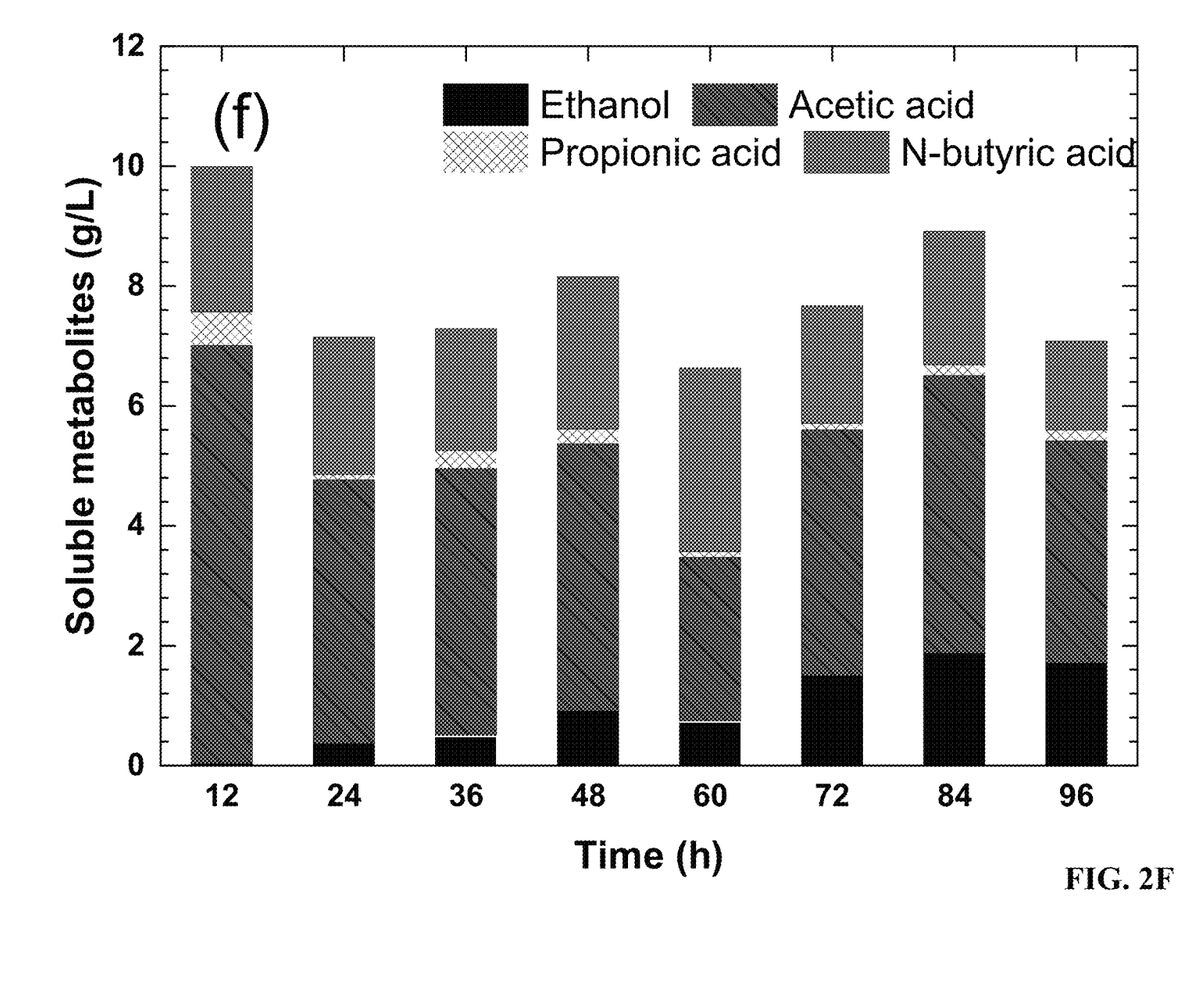

Referring to FIG. 1E, except for the experimental group with pH=5, the pH value of the other experimental groups decreases quickly during 0-24 h, which may be due to the accumulation of volatile fatty acids produced by photosynthetic bacteria HAU-M1. The pH value of the experimental group decreased faster than that of the control group, since the pH (4.8) of the buffer in the control group was adjusted by NaOH, while the buffer in the experimental group was prepared by $Na_2HPO_4/NaH_2PO_4$. The pH values increase slowly after 48 h when the pH value is higher than 6.0. The photosynthetic bacteria degrade the volatile fatty acids in the fermentation broth for produce hydrogen, and the decrease of volatile fatty acids leads to the increase of pH values. The pH values decreases continuously when the pH value is lower than 6. The low pH values weaken the activity of photosynthetic bacteria, or even kill the photosynthetic bacteria.

TABLE 2

| Parameters | Variance analysis | | | | |
| --- | --- | --- | --- | --- | --- |
| | Hydrogen content | Hydrogen production rate | Cumulative hydrogen production | pH value | Reducing sugar concentration |
| F | 0.29 | 0.52 | 1.79 | 23.14 | 1.29 |
| P-value | 0.92 | 0.76 | 0.13 | 9.46E-12 | 0.29 |
| F crit | 2.41 | 2.41 | 2.41 | 2.41 | 2.41 |

Table 2 shows the significance of different pH values on the hydrogen content, hydrogen production rate, cumulative hydrogen production, pH value of the buffer solution, and reducing sugar concentration of photo-fermentation biohydrogen production. The results show that P value (9.46E-12) of the pH of the fermentation broth is far less than 0, and F value (23.14) is far higher than F crit value (2.41), indicating that the fermentation broth is significantly affected by the pH values of buffer solution. The effect of pH value on the parameters in descending order is cumulative hydrogen production, reducing sugar concentration, and hydrogen production rate. The pH value has the least influence (P 0.92) on the hydrogen content.

2.2 Effect of pH Values of Buffer Solution on the Production of Volatile Fatty Acids.

FIGS. 2A-2F are bar graphs illustrating the effect of pH values of the buffer solution on soluble metabolites, in which the soluble metabolites reflect the changes in the metabolites during photo-fermentation biohydrogen production. The main soluble metabolites are acetic acid and butyric acid, and followed by a little of propionic acid and ethanol. Referring to chemical equations 5 and 7, remarkable biohydrogen production is observed when the metabolic pathways are acetic acid and butyric acid. Referring to chemical equations 6 and 8, the hydrogen was not generated and sugars are consumed in large quantities when the metabolites are propionic acid and ethanol as ethanol has negative effect of the growth of photosynthetic bacteria. High total amount of volatile fatty acids are found during 12-24 h, because the volatile fatty acids have not been converted into hydrogen by photosynthetic bacteria. In 36-60 hours, the total amount of soluble metabolites in the fermentation broth was relatively stable, indicating that the production rate of the volatile fatty acids equal the consumption rate of the volatile fatty acids.

2.3 Effect of Buffer Solution on Kinetic Parameters.

TABLE 3

Kinetic parameters

| pH value | $P_{max}$ (mL) | $R_m$ (mL/h) | λ (h) | $R^2$ | $R_{overall}$ (mL/h) | Hydrogen production yield (mL/g) |
|---|---|---|---|---|---|---|
| 5 | 204.50 | 5.78 | 22.79 | 0.9965 | 2.12 | 40.63 |
| 5.5 | 394.02 | 17.92 | 29.48 | 0.9975 | 4.11 | 78.85 |
| 6 | 673.22 | 23.17 | 24.83 | 0.9910 | 6.91 | 132.69 |
| 6.5 | 530.83 | 28.05 | 30.66 | 0.9968 | 5.54 | 106.30 |
| 7 | 340.28 | 15.41 | 31.39 | 0.9980 | 3.51 | 67.33 |
| Control group | 506.79 | 26.37 | 31.15 | 0.9990 | 5.30 | 101.73 |

Kinetic parameters of biohydrogen production are used to simulate, calculate the behavior of photo-fermentation biohydrogen production, and digitize the biohydrogen production process, so that the hydrogen production can be better understand. Referring to Table 3, the maximum cumulative hydrogen production ($P_{max}$) increases, reaches the maximum value of 673.22 mL at pH 6, and then decreases. The calculated maximum cumulative hydrogen production value of 673.22 mL is in good agreement with the actual value (663.45 mL). The maximum hydrogen production rate ($R_m$) show the same trend as the accumulative hydrogen production, which indicates that pH value has a great impact on the maximum hydrogen production per unit time. A minimum delay time was achieved at pH value of 5, which was because the cellulase has the best activity at pH value of 5 and is quickly converted into sugar. Biohydrogen production is carried out soon at pH value of 6, which is due to the photosynthetic bacteria and cellulase have good activity at pH value of 6. The correlation coefficients ($R^2$) are more than 0.99, close to 1, which indicates that the kinetic parameters of biohydrogen production described the process photo-fermentation biohydrogen production well. The overall hydrogen production rate ($R_{overall}$) reflects the hydrogen production performance of the whole biohydrogen production process, which is obtained by the ratio of the cumulative hydrogen production to the time. The overall hydrogen production rate increases and then decreases with the increase of the pH value. The pH values of the buffer solution has no evidence relationship with the biohydrogen production. The maximum hydrogen production is 132.69 mL/g at pH of 6.

2.4 Effect of pH Values of Buffer Solution on the Energy Conversion Efficiency

Figure 3:
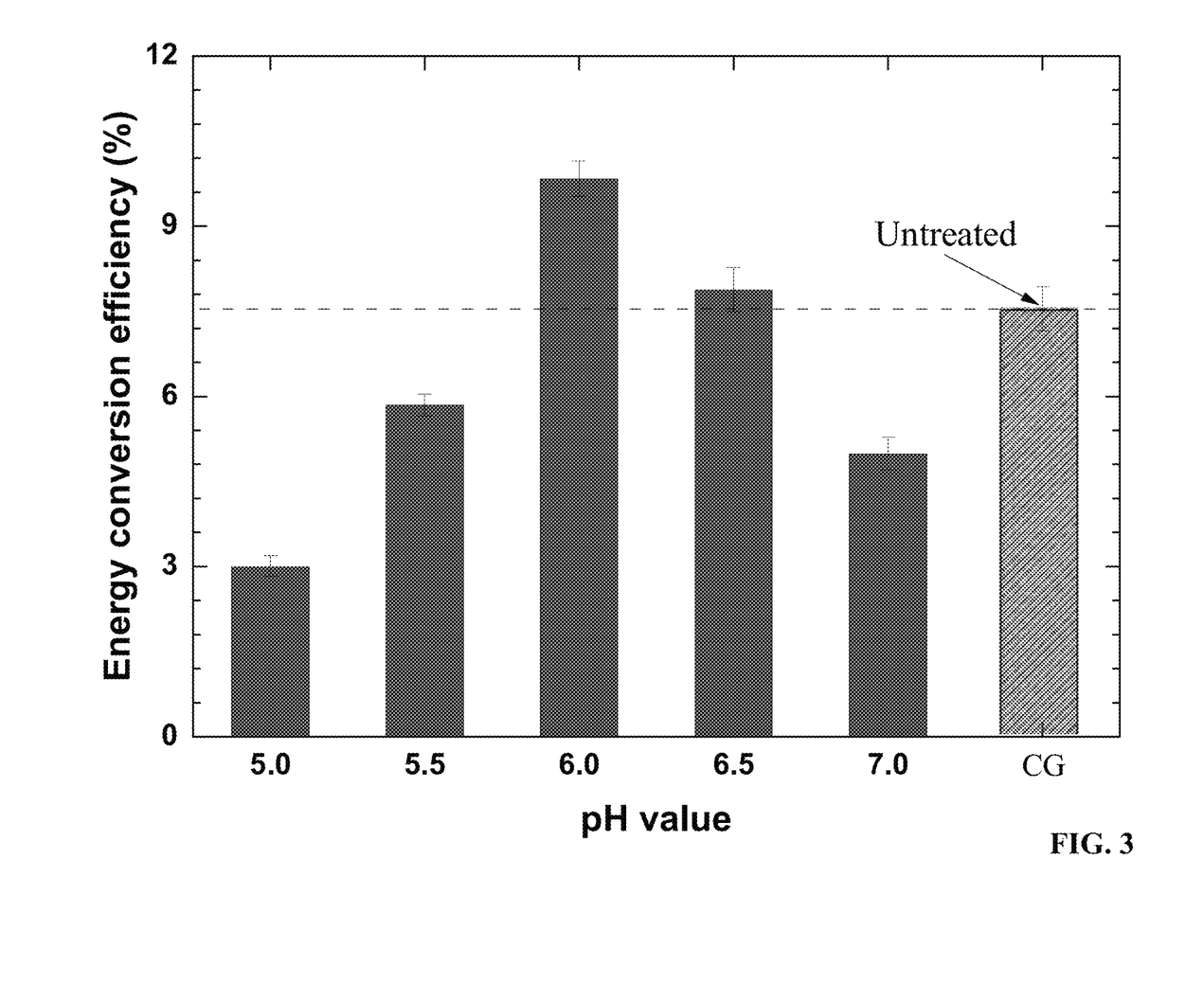
FIG. 3 are bar graphs illustrating the effect of pH values of buffer solution on energy conversion efficiency.

FIG. 3 shows bar graphs illustrating the effect of pH values of buffer solution on energy conversion efficiency. Referring to FIG. 3, the energy conversion efficiency increases and then decreases as the pH value increases. This significant variety is caused by the comprehensive effect of pH values on photosynthetic bacteria and cellulase.

3. Conclusion

Buffer solution $Na_2HPO_4/NaH_2PO_4$ with different initial pH values has an impact on photo-fermentation biohydrogen production. The maximum hydrogen production of 132.69 mL/g, the hydrogen content of 53.88%, and the energy conversion efficiency of 9.84% are observed at pH value of 6. The results of one-way ANOVA show that the pH value has a significant impact on the fermentation broth and cumulative hydrogen production. The analysis results provide technical support for biohydrogen production.

It will be obvious to those skilled in the art that changes and modifications may be made, and therefore, the aim in the appended claims is to cover all such changes and modifications.

What is claimed is:
1. A method, comprising:
   1. mixing a hydrogen production medium and a buffer solution $Na_2HPO_4/NaH_2PO_4$ having a pH value of between 5 and 9, to yield a first mixture;
   2. adding corn stalk powder and cellulase to the first mixture and mixing, to yield a second mixture;
   3. culturing photosynthesis bacteria in a culture media until a late exponential phase of growth, adding a suspension of the photosynthesis bacteria at the late exponential phase of growth to the second mixture, to yield a third mixture, wherein the photosynthesis bacteria comprise *Rhodospirillum cristatum*, *Rhodopseudomonas capsulatus*, *Rhodopseudomonas palustris*, *Rhodobacter sphaeroides*, and *Rhodobacter capsularis*; and
   4. sealing the third mixture and allowing for photo-fermentation biohydrogen production under anaerobic fermentation conditions.

2. The method of claim 1, wherein a volume of the $Na_2HPO_4/NaH_2PO_4$ buffer is 110-130 mL, and a dry weight of the corn stalk powder is 5 g.

3. The method of claim 2, wherein the hydrogen production medium comprises 0.4 g/L $NH_4Cl$, 0.5 g/L $K_2HPO_4$, 2 g/L NaCl, 0.1 g/L yeast extract, 0.2 g/L $MgCl_2$, and 3.56 g/L sodium glutamate.

4. The method of claim 1, wherein the cellulase is a liquid enzyme preparation; the cellulase has a volume of 4-6 mL and an enzyme activity of 51 FPU/mL; the suspension of the photosynthesis bacteria has a volume of 20-40 mL.

5. The method of claim 2, wherein the cellulase is a liquid enzyme preparation; the cellulase has a volume of 4-6 mL and an enzyme activity of 51 FPU/mL; the suspension of the photosynthesis bacteria has a volume of 20-40 mL.

6. The method of claim 3, wherein the cellulase is a liquid enzyme preparation; the cellulase has a volume of 4-6 mL and an enzyme activity of 51 FPU/mL; the suspension of the photosynthesis bacteria has a volume of 20-40 mL.

7. The method of claim 4, wherein *Rhodospirillum cristatum, Rhodopseudomonas capsulatus, Rhodopseudomonas palustris, Rhodobacter sphaeroides*, and *Rhodobacter capsularis* are mixed in a volume ratio of 27:25:28:9:11; the number of viable *Rhodospirillum cristatum* in the suspension is $12.0 \times 10^8$ cells/mL; the number of viable *Rhodopseudomonas capsulatus* in the suspension is $11.0 \times 10^8$ cells/mL; the number of viable *Rhodopseudomonas palustris* in the suspension is $12.5 \times 10^8$ cells/mL; the number of viable *Rhodobacter sphaeroides* in the suspension is $4.0 \times 10^8$ cells/mL; and the number of viable *Rhodobacter capsularis* in the suspension is $5.0 \times 10^8$ cells/mL.

8. The method of claim 5, wherein *Rhodospirillum cristatum, Rhodopseudomonas capsulatus, Rhodopseudomonas palustris, Rhodobacter sphaeroides*, and *Rhodobacter capsularis* are mixed in a volume ratio of 27:25:28:9:11; the number of viable *Rhodospirillum cristatum* in the suspension is $12.0 \times 10^8$ cells/mL; the number of viable *Rhodopseudomonas capsulatus* in the suspension is $11.0 \times 10^8$ cells/mL; the number of viable *Rhodopseudomonas palustris* in the suspension is $12.5 \times 10^8$ cells/mL; the number of viable *Rhodobacter sphaeroides* in the suspension is $4.0 \times 10^8$ cells/mL; and the number of viable *Rhodobacter capsularis* in the suspension is $5.0 \times 10^8$ cells/mL.

9. The method of claim 6, wherein *Rhodospirillum cristatum, Rhodopseudomonas capsulatus, Rhodopseudomonas palustris, Rhodobacter sphaeroides*, and *Rhodobacter capsularis* are mixed in a volume ratio of 27:25:28:9:11; the number of viable *Rhodospirillum cristatum* in the suspension is $12.0 \times 10^8$ cells/mL; the number of viable *Rhodopseudomonas capsulatus* in the suspension is $11.0 \times 10^8$ cells/mL; the number of viable *Rhodopseudomonas palustris* in the suspension is $12.5 \times 10^8$ cells/mL; the number of viable *Rhodobacter sphaeroides* in the suspension is $4.0 \times 10^8$ cells/mL; and the number of viable *Rhodobacter capsularis* in the suspension is $5.0 \times 10^8$ cells/mL.

10. The method of claim 4, wherein in 4), the photo-fermentation biohydrogen production is carried out at a temperature of 28-32° C. and a light intensity of 2800-3200 Lux.

11. The method of claim 5, wherein in 4), the photo-fermentation biohydrogen production is carried out at a temperature of 28-32° C. and a light intensity of 2800-3200 Lux.

12. The method of claim 6, wherein in 4), the photo-fermentation biohydrogen production is carried out at a temperature of 28-32° C. and a light intensity of 2800-3200 Lux.

* * * * *